United States Patent [19]

Fukushige et al.

[11] Patent Number: 5,235,096
[45] Date of Patent: Aug. 10, 1993

[54] HYDROXYBENZENESULFONE COMPOUND HAVING A POLYMERIZABLE GROUP AND PROCESS FOR PRODUCING THE SAME

[75] Inventors: Yuuichi Fukushige; Masato Satomura, both of Shizuoka, Japan

[73] Assignee: Fuji Photo Film Co., Ltd., Kanagawa, Japan

[21] Appl. No.: 851,162

[22] Filed: Mar. 13, 1992

[30] Foreign Application Priority Data

Mar. 14, 1991 [JP] Japan ................................ 3-049705

[51] Int. Cl.⁵ ............................................ C07L 205/00
[52] U.S. Cl. ............................................ 560/221
[58] Field of Search ................................ 560/221

[56] References Cited

U.S. PATENT DOCUMENTS 4,194,052 3/1980 Lewis et al. ........................ 560/21
4,990,653 2/1991 Hayakawa et al. ............... 560/21

FOREIGN PATENT DOCUMENTS 8079970 5/1983 Japan .
2234051 10/1987 Japan .
2102782 2/1983 United Kingdom .

Primary Examiner—Paul J. Killos
Attorney, Agent, or Firm—Sughrue, Mion, Zinn, Macpeak & Seas

[57] ABSTRACT

A hydroxybenzenesulfone compound represented by the following formula (I):

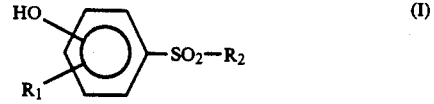

wherein all symbol are defined in the specification, and a process for producing the compound is disclosed. Further, a process for producing a hydroxybenzenesulfone compound having an alcoholic hydroxyl group and represented by the following formula (III):

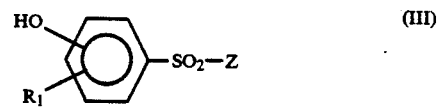

wherein all symbols are defined in the specification, comprising the step of oxidizing a hydroxyalkylthiophenol compound having an alcoholic hydroxyl group is disclosed. Furthermore a process for producing a compound represented by the following formula (IV):

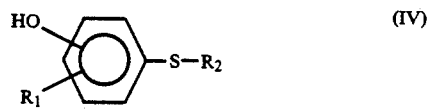

wherein all symbols are defined in the specification, comprising the step of reacting a hydroxyalkylthiophenol compound with an acrylic acid halide or a methacrylic halide in a polar solvent is disclosed.

5 Claims, No Drawings

HYDROXYBENZENESULFONE COMPOUND HAVING A POLYMERIZABLE GROUP AND PROCESS FOR PRODUCING THE SAME

FIELD OF THE INVENTION

This invention relates to a hydroxybenzenesulfone compound having a polymerizable group, which is useful as a polymerizable monomer for use in recording materials, and to a process for the production thereof.

BACKGROUND OF THE INVENTION

Several hydroxybenzenesulfone compounds are known as compounds for use in recording materials. However, a hydroxybenzenesulfone compound having a polymerizable group has not been known.

SUMMARY OF THE INVENTION

An object of this invention is to provide a novel hydroxybenzenesulfone compound having a polymerizable group, which is useful as a polymerizable monomer for use in recording materials, and a process for the production thereof.

Particularly, in accordance with the present invention, there is provided a hydroxybenzenesulfone compound represented by the following formula (I):

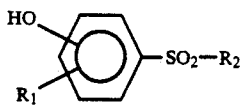

wherein $R_1$ represents a hydrogen atom, a halogen atom, an alkyl group, an alkoxy group or an aryl group, and $R_2$ represents an acryloyloxyalkyl group or methacryloyloxyalkyl group.

The present invention also provides a process for producing a hydroxybenzenesulfone compound having an alcoholic hydroxyl group and represented by the following formula (III):

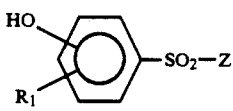

wherein $R_1$ is the same group defined in formula (I) and Z is a hydroxyalkyl group;
comprising the step of oxidizing a hydroxyalkylthiophenol compound having an alcoholic hydroxyl group and represented by the following formula (II):

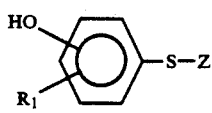

wherein $R_1$ is the same group defined in formula (I) and Z is a hydroxyalkyl group.

The present invention further provides a process for producing a hydroxybenzenesulfone compound having a polymerizable group and represented by the above formula (I) comprising reacting a hydroxybenzenesulfone compound having an alcoholic hydroxyl group and represented by the above formula (III) with an acrylic acid or methacrylic acid halide in a polar solvent.

The present invention furthermore provides a process for producing a compound represented by the following formula (IV):

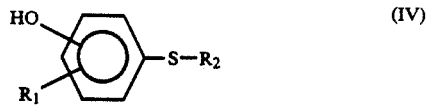

wherein $R_1$, $R_2$ and Z are the same group defined above; comprising the step of reacting a hydroxyalkylthiophenol compound having an alcohol hydroxy group and represented by formula (II) with an acrylic acid halide or a methacrylic halide in a polar solvent.

The present invention still furthermore provides a process for producing a hydroxybenzenesulfone compound having a polymerizable group and represented by the above formula (I) comprising oxidizing a compound represented by the above formula (IV).

Other objects and advantages will be made apparent as the description progresses.

DETAILED DESCRIPTION OF THE INVENTION

Examples of the halogen atom represented by R of formula (I) include chlorine atom and fluorine atom. As the alkyl and alkoxy group represented by $R_1$ of formula (I), those containing 1 to 5 carbon atoms are preferred. The $R_1$ group may preferably be located at the ortho or meta position in relation to the hydroxy group.

In formula (I), the group $R_2$ may preferably be an alkyl group which contains an acryloyloxy or a methacryloyloxy group and has 5 to 20 carbon atoms. The group $R_2$ may contain two or more polymerizable groups. When the group $R_2$ contains two or more polymerizable groups, they may be either acryloyloxy groups, methacryloyloxy groups or a combination of acryloyloxy group(s) and methacryloyloxy group(s). The group $R_2$ may further contain a substituent group such as an alkoxy group (e.g., methoxy, ethoxy), an aryloxy group (e.g., phenoxy), a halogen atom, an aryl group or the like; or an oxygen atom, a sulfur atom or a phenylene group. When the group $R_2$ has the substituent, the number of the substituent(s) is preferably 1 or 2. In addition, the —$SO_2$— $R_2$ group may preferably be located at the ortho or para position in relation to the hydroxyl group. The para position is more preferred.

Among the hydroxybenzenesulfone compounds represented by formula (I), those represented by the following formulae (V) and (VI) are preferred:

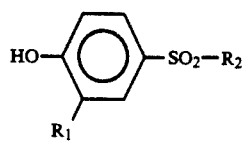

wherein $R_1$ and $R_2$ are the same groups defined in formula (I); and

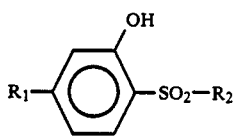

(VI)

wherein R₁ and R₂ are the same groups defined in formula (I).

Specific examples of the group represented by R₂ include acryloyloxyethyl, methacryloyloxyethyl, 3-acryloyloxypropyl, 3-methacryloyloxypropyl, 2-acryloyloxypropyl, 2-methacryloyloxypropyl, 4-acryloyloxybutyl, 4-methacryloyloxybutyl, 6-acryloyloxyhexyl, 6-methacryloyloxyhexyl, 8-acryloyloxyoctyl, 8-methacryloyloxyoctyl, 10-acryloyloxydecyl, 10-methacryloyloxydecyl, 4-(acryloyloxymethyl)benzyl, 4-(methacryloyloxymethyl)benzyl, 3-(acryloyloxymethyl)benzyl, 3-(methacryloyloxymethyl)benzyl, 2-(acryloyloxymethyl)benzyl, 2-(methacryloyloxymethyl)benzyl, 12-methacryloyloxydodecyl, 2-(acryloyloxyethoxy)ethyl, 2-(methacryloyloxyethoxy)ethyl, 3-(3-acryloyloxypropoxy)propyl)propyl, 2,3-bis(acryloyloxy)propyl, 2,3-bis(methacryloyloxy)propyl and the like.

Specific examples of the hydroxybenzenesulfone compound represented by formula (I) include 1-(4-hydroxybenzenesulfonyl)-2-acryloyloxyethane, 1-(4-hydroxybenzenesulfonyl)-2-methacryloyloxyethane, 1-(4-hydroxybenzenesulfonyl)-3-acryloyloxypropane, 1-(4-hydroxybenzenesulfonyl)-3-methacryloyloxypropane, 1-(4-hydroxybenzenesulfonyl)-2-acryloyloxypropane, 1-(4-hydroxbenzenesulfonyl)-2-methacryloyloxypropane, 1-(4-hydroxyenzenesulfonyl)-4-acryloyloxybutane, 1-(4-hydroxybenzenesulfonyl)-4-methacryloyloxybutane, 1-(4-hydroxybenzenesulfonyl)-5-acryloyloxyhexane, 1-(4-hydroxybenzenesulfonyl)-6-methacryloyloxyhexane, 1-(4-hydroxybenzenesulfonyl)-8-acryloyloxyoctane, 1-(4-hydroxybenzenesulfonyl)-8-methacryloyloxyoctane, 1-(4-hydroxybenzenesulfonyl)-10-acryloyloxydecane, 1-(4-hydroxybenzenesulfonyl)-10-methacryloyloxdecane, 1-(4-hydroxybenzenesulfonyl)-2-[2-(methacryloyloxyethoxy)]ethane, 1-(4-hydroxybenzenesulfonyl)-3-[3-(methacryloyloxypropoxy)]propane, 1-(4-hydroxybenzenesulfone)-3-[2,3-bis(methacryloyloxy)]propane, 1-(3-isopropyl-4-hydroxybenzenesulfonyl)-2-methacryloyloxyethane, 1-(3-isopropyl-4-hydroxybenzenesulfonyl)-2-acryloyloxyethane, 1-(3-isopropyl-4-hydroxybenzenesulfonyl)-3-methacryloyloxypropane, 1-(3-isopropyl-4-hydroxybenzenesulfonyl)-3-acryloyloxypropane, 1-(3-isopropyl-4-hydroxybenzenesulfonyl)-6-methacryloyloxyhexane, 1-(3-isopropyl-4-hydroxybenzenesulfonyl)-6-acryloyloxyhexane, 1-(3-chloro-4-hydroxybenzenesulfonyl)-3-methacryloyloxypropane, 1-( 3-chloro-4-hydroxybenzenesulfonyl)-3-acryloyloxypropane, 1-(3-chloro-4-hydroxybenzenesulfonyl)-6-methacryloyloxyhexane, 1-(3-chloro-4-hydroxybenzenesulfonyl)-6-acryloyloxyhexane, 1-(3-chloro-4-hydroxybenzenesulfonyl)-8-methacryloyloxyoctane, 1-(3-chloro-4-hydroxybenzenesulfonyl)-8-acryloyloxyoctane, 1-(4-chloro-2-hydroxybenzenesulfonyl)-6-methacryloyloxyhexane, 1-(4-chloro-2-hydroxybenzenesulfonyl)-6-acryloyloxyhexane, 1-(3-methyl-4-hydroxybenzenesulfonyl)-6-methacryloyloxyhexane, 1-(3-methyl-4-hydroxybenzenesulfonyl)-6-acryloyloxyhexane, 1-(3-methyl-4-hydroxybenzenesulfonyl)-8-methacryloyloxyoctane, 1-(3-methyl-4-hydroxybenzenesulfonyl)-8-acryloyloxyoctane, 1-(3-phenyl-4-hydroxybenzenesulfonyl)-3-methacryloyloxypropane, 1-(3-phenyl-4-hydroxybenzenesulfonyl)-3-acryloyloxypropane, 1-(3-phenyl-4-hydroxybenzenesulfonyl)-6-methacryloyloxyhexane, 1-(3-phenyl-4-hydroxybenzenesulfonyl)-6-acryloyloxyhexane, 1-(3-phenyl-4-hydroxybenzenesulfonyl)-8-methacryloyloxyoctane, 1-(3-phenyl-4-hydroxybenzenesulfonyl)-8-acryloyloxyoctane, 2-chloro-4-[2-(β-methacryloyloxyethoxy)ethylsulfonyl]phenol, 2-chloro-4-[2-(β-acryloyloxyethoxy)ethylsulfonyl]phenol, 2-methyl-4-[2-(β-methacryloyoxyethoxy)ethylsulfonyl]phenol, 2-methyl-4-[2-(β-acryloyloxyethoxy)ethylsulfonyl]phenol, 2-phenyl-4-[2-(β-methacryloyloxyethoxy)ethylsulfonyl]phenol, 2-phenyl-4-[2-(β-acryloyoxyethoxy)ethylsulfonyl]phenol, 2-isopropyl-4-[2-(β-methacryloyloxyethoxy)ethylsulfonyl]phenol, 2-isopropyl-4-[2-(β-acryloyloxyethoxy)ethylsulfonyl]phenol, and the like.

In the aforementioned formulae (II) and (III), the group Z may preferably be a hydroxyalkyl group having 2 to 18 carbon atoms. Specific examples thereof include hydroxyalkyl groups obtained by eliminating an acryloyl or methacryloyl group from the specific examples listed above for R₂.

According to the present invention, the process for the production of the compound represented by formula (III) is effected by oxidizing the hydroxyalkylthiophenol compound of formula (II) containing an alcoholic hydroxy group. The oxidation reaction may be carried out using conventional means. Many methods for the oxidation of sulfides are known, as well as several processes for their production. Such methods and processes have been described in detail, for instance, by H. S. Schultz et al. in *J. Org. Chem.*, Vol. 28, P. 1140 (1963) and by C. G. Overberger et al. in *J. Am. Chem. Soc.*, vol. 72, p. 2856 (1950). In general, the oxidation reaction is carried out using hydrogen peroxide. The compound of formula (III) is directly obtained by oxidizing the compound of formula (II) in the presence of an acid catalyst, such as acetic acid which is also to be used as a solvent, and a metal catalyst, such as Mo, Ti, Cr, W and V. In this instance, sulfoxides are formed under neutral condition in the absence of a catalyst. However, these compounds are also useful in the present invention. The reaction temperature may range from 50° to 80° C., preferably from 60° to 75° C.

According to one embodiment of the present invention, the process for the production of the compound represented by formula (I) is carried out using a selective esterification method. The selective esterification method is an esterification technique by which an alcoholic hydroxy group in a phenolic compound having a substituent containing an alcoholic hydroxy group is exclusively allowed to react without allowing the phenolic hydroxy group thereof to react, as disclosed, for example, in Japanese Patent Application Nos. Hei-3-2131 and Hei-3-20095. In this method, a phenol compound having an alcoholic hydroxide group and represented by formula (III) is allowed to react with an acrylic acid halide or a methacrylic acid halide in a polar solvent in the presence of an amide or urea compound. A preferred example of the halogen atom of the acid halide includes chlorine atom.

In the inventive process for the production of the compound of formula (I), the polar solvent to be used may preferably be selected from nitryl solvents, halogenated hydrocarbon solvents, ethers, amide solvents, ketone solvents, ester solvents, aromatic hydrocarbons and the like, with specific examples including acetonitrile, methylene chloride, acetone, chloroform, ethyl acetate, tetrahydrofuran, dioxane, N,N-dimethylacetamide, N-methylpyrrolidone and the like.

The inventive process for the production of the compound of formula (I) is carried out in the presence of an amide compound or a urea compound as a deoxidizer. A tertiary amide compound or a urea compound in which all the nitrogen atoms have substituent groups may preferably be used as the amide or urea compound. Specific and preferred examples of the amide or urea compound include N,N-dimethylacetamide, N,N-diethylacetamide, N,N-dimethylpropioamide, N-methylpyrrolidone, tetramethylurea, tetraethylurea, N-methylacetanilide and the like. These deoxidizers may also be used as a solvent.

In the practice of the process of the present invention, an acid halide may preferably be used in an amount of from 1.0 to 10.0 molar equivalent, more preferably be used from 1.0 to 5.0 molar equivalent, in relation to 1.0 mole of the compound represented by formula (III). The amide or urea compound may preferably be used in a molar equivalent of 1.0 or more in relation to 1.0 mole of the acid halide used. The reaction temperature may preferably be in the range of from $-10°$ C. to $100°$ C., more preferably from $5°$ C. to $50°$ C.

According to the present invention, the process for the production of the compound represented by formula (IV) is effected by reacting the hydroxyalkylthiophenol compound having an alcoholic hydroxy group and represented by formula (II) with an acrylic acid halide or a methacrylic acid halide in a polar solvent in, for example, a selective esterification method as described above in relation to the process for the production of compound represented by formula (I). A preferred example of the halogen atom of the acrylic acid or methacrylic acid include chlorine atom.

The polar solvent to be used in this reaction may preferably be selected from nitryl solvents, halogenated hydrocarbon solvents, ethers, amide solvents, ketone solvents, ester solvents, aromatic hydrocarbons and the like, with specific examples including acetonitrile, methylene chloride, acetone, chloroform, ethyl acetate, tetrahydrofuran, dioxane, N,N-dimethylacetamide, N-methylpyrrolidone and the like.

The process for the production of the compound of formula (IV) is carried out in the presence of an amide compound or a urea compound as a deoxidizer. A tertiary amide compound or a urea compound in which all the nitrogen atoms have substituent groups may preferably be used as the amide or urea compound. Specific and preferred examples of the amide or urea compound include N,N-dimethylacetamide, N,N-diethylacetamide, N,N-dimethylpropioamide, N-methylpyrrolidone, tetramethylurea, tetraethylurea, N-methylacetanilide and the like. These deoxidizers may also be used as a solvent.

In the practice of the process of the present invention, the acrylic acid halide or the methacrylic acid halide may preferably be used in an amount of from 1.0 to 10.0 molar equivalent, more preferably be used from 1.0 to 5.0 molar equivalent, in relation to 1.0 mole of the compound represented by formula (II). The amide or urea compound may preferably used in a molar equivalent of 1.0 or more in relation to 1.0 mole of the acid halide used. The reaction temperature may preferably be in the range of from $-10°$ C. to $100°$ C., more preferably from $5°$ C. to $50°$ C.

According to another embodiment of the present invention, the process for the production of the compound represented by formula (I) is carried out by oxidizing the compound of formula (IV) with an oxidizing agent such as hydrogen peroxide. The oxidation reaction may be carried out using a conventional manner such as the method described above in relation to the oxidation method of the process for the production of the compound represented by formula (II). In general, the oxidation reaction is carried out using hydrogen peroxide. The reaction temperature may preferably be in the range of from $50°$ to $80°$ C., more preferably from $60°$ to $75°$ C.

The hydroxybenzenesulfone compound of the present invention is useful as an electron accepting compound to be used in a pressure-sensitive, heat-sensitive, light-sensitive recording material or the like each of which color formation reaction is utilized. Examples of the recording material to which the hydroxybenzenesulfone compound of the present invention can be used are disclosed, for example, in British Patent 2140449, U.S. Pat. No. 4,480,052, U.S. Pat. No. 4,436,920, JP-B-60-23992 (the term "JP-B" as used herein means an "examined Japanese Patent Publication"), JP-A-57-179836 (the term "JP-A" as used herein means an "unexamined published Japanese Patent Application"), JP-A-60-123556, JP-A-60-123557.

The hydroxybenzenesulfone compound of the present invention is also useful as an electron accepting compound to be used in a light-sensitive heat-sensitive recording material which utilizes polymerizability and color forming property of a compound. Examples of the recording material of this type are disclosed, for example, in JP-A-3-72358 and JP-A-387827.

An amount of the hydroxybenzenesulfone compound of the present invention in these types of the recording material is not particularly limited, but it is generally from 1 to 100 mole per 1 mole of an electron donating colorless dye employed therein.

The hydroxybenzenesulfone compound of the present invention is highly useful as an electron accepting compound and the process of the present invention is advantageous in its simplicity and easiness of handling. Further, the hydroxybenzenesulfone compound of the present invention gives a Pka value different from conventional electron accepting compounds and its $-SO_2-$ group is hardly undergone hydrolysis, thus it is advantageous.

Examples of the present invention are given below by way of illustration and not by way of limitation. Unless otherwise noted, the term "%" as used herein means "% by weight".

EXAMPLE 1

A 16 g portion of 4-hydroxybenzene-(2-hydroxyethyl)thioether was dissolved in 40 ml of acetic acid, and the solution was stirred at $65°$ C. To this solution, 10 ml of a 30% hydrogen peroxide was added dropwise. After stirring for 2 hours, the resulting solution was poured in ice-cold water, extracted with ethyl acetate, washed twice with water and dried to remove the water and then the ethyl acetate was distilled off therefrom. To 20 ml acetonitrile solution containing 10 g of the thus concentrated sample were added in a dropwise manner while stirring, 25 ml of N-methylpyrrolidone and then 15.5 g of methacrylic acid chloride. After stirring the mixture at 40° C. for 5 hours to proceed the reaction, the resulting reaction mixture was poured in ice-cold water. Thereafter, the resulting precipitated crystals were collected by filtration, and then recrystallized from ethyl acetate/n-hexane to obtain 1-(4-hydroxybenzenesulfonyl)-2-acryloyloxyethane (melting point: 91°-92° C.

EXAMPLE 2

The reaction of Example 1 was repeated except that 4-hydroxybenzene-(3-hydroxypropyl)thioether was used instead of 4-hydroxybenzene-(2-hydroxyethyl)-thioether. The resulting reaction mixture was poured in ice-cold water, and the resulting precipitated crystals were collected by filtration, and then recrystallized from ethyl acetate/n-hexane to obtain 1-(4-hydroxybenzenesulfonyl)-3-methacryloyloxypropane.

EXAMPLE 3

The reaction of Example 1 was repeated except that 2-methyl-4-(6-hydroxyhexylthio)phenol was used instead of 4-hydroxybenzene-(2-hydroxyethyl)thioether. The resulting reaction mixture was poured in ice-cold water, extracted with ethyl acetate, washed twice with water and dehydrated and dried to remove the water, and then the ethyl acetate was distilled off therefrom. The thus concentrated sample was purified with silica gel column chromatography to obtain 1-(3-methyl-4-hydroxybenzenesulfonyl)-6-methacryloyloxyhexane (melting point: 84°-85° C.).

EXAMPLE 4

The reaction and purification of Example 3 were repeated except that 2-chloro-4-(6-hydroxyhexylthio)-phenol was used instead of 2-methyl-4-(6-hydroxyhexylthio)phenol to thereby obtain 1-(3-chloro-4-hydroxybenzenesulfonyl)-6-methacryloyloxyhexane (melting point: 86°-87° C.).

EXAMPLE 5

The reaction and purification of Example 3 were repeated except that 2-isopropyl-4-(6-hydroxyhexylthio)phenol was used instead of 2-methyl-4-(6-hydroxyhexylthio)phenol to thereby obtain 1-(3-isopropyl-4-hydroxybenzenesulfonyl)-6-methacryloyloxyhexane.

EXAMPLE 6

The reaction and purification of Example 3 were repeated except that 2-phenyl-4-(6-hydroxyhexylthio)-phenol was used instead of 2-methyl-4-(6-hydroxyhexylthio)phenol to thereby obtain 1-(3-phenyl-4-hydroxybenzenesulfonyl)-6-methacryloyloxyhexane (melting point: 100° C.).

EXAMPLE 7

A 25 ml portion of N-methylpyrrolidone was added to 20 ml of an acetonitrile solution containing 10 g of 2-chloro-4-(6-hydroxyhexylthio)phenol with stirring and 15.5 g of acrylic chloride was further added dropwise to the resulting solution. After allowing to proceed the reaction for 5 hours at 40° C. with stirring, the resulting solution was poured in ice-cold water, extracted with ethyl acetate, washed twice with water and dehydrated and dried to remove the water, and then the ethyl acetate was distilled off therefrom. To 40 ml acetic acid solution containing 12 g of the thus concentrated sample was added 10 ml of acetonitrile and the resulting solution was stirred at 65° C., followed by addition of 10 ml of a 35% hydrogen peroxide. After 1 hour, 10 ml of a 35% hydrogen peroxide was further added to the resulting solution in a dropwise manner. After allowing to proceed the reaction for additional 2 hours, the resulting solution was poured in ice-cold water, extracted with ethylacetate, washed twice with water and dehydrated and dried to remove the water, and then the ethyl acetate was distilled off therefrom. The thus concentrated sample was purified with silica gel column chromatography to obtain 1-(3-chloro-4-hydroxybenzenesulfonyl)-6-acryloyloxyhexane.

EXAMPLE 8

The reaction and purification of Example 7 were repeated except that 2-phenyl-4-(3-hydroxypropylthio)-phenol was used instead of 2-chloro-4-(6-hydroxyhexylthio)phenol to thereby obtain 1-(3-phenyl-4-hydroxybenzenesulfonyl)-3-methacryloyloxypropane.

EXAMPLE 9

The reaction and purification of Example 7 were repeated except that 2-chloro-4-(6-hydroxyhexylthio)-phenol was used instead of 2-chloro-4-(6-hydroxyhexylthio)phenol to thereby obtain 1-(3-chloro-4-hydroxybenzenesulfonyl)-6-methacryloyloxyhexane (melting point: 86°-87° C.).

EXAMPLE 10

The reaction and purification of Example 7 were repeated except that 2-methyl-4-(6-hydroxyhexylthio)-phenol was used instead of 2-chloro-4-(6-hydroxyhexylthio)phenol to thereby obtain 1-(3-methyl-4-hydroxybenzenesulfonyl)-6-methacryloyloxyhexane (melting point: 84°-85° C.).

While the invention has been described in detail and with reference to specific embodiments thereof, it will be apparent to one skilled in the art that various changes and modifications can be made therein without departing from the spirit and scope thereof.

What is claimed is:

1. A hydroxybenzenesulfone compound having a polymerizable group and represented by the following formula (I):

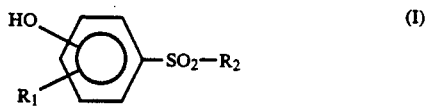

wherein $R_1$ represents a hydrogen atom, a halogen atom, an alkyl group, an alkoxy group or an aryl group, and $R_2$ represents an acryloyloxyalkyl group or a methacryloyloxyalkyl group.

2. The hydroxybenzenesulfone compound of claim 1, wherein said hydroxybenzenesulfone compound is represented by the following formula (V):

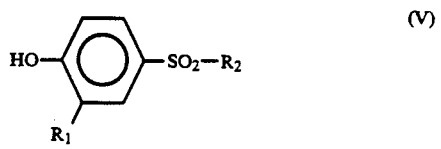

wherein $R_1$ and $R_2$ have the same meaning as defined in formula (I) in claim 1.

3. The hydroxybenzenesulfonyl compound of claim 2, wherein said compound is selected from the group consisting of 1-(4-hydroxybenzenesulfonyl)-2-acryloyloxyethane, 1-(4-hydroxybenzenesulfonyl)-2-methacryloyloxyethane, 1-(4-hydroxybenzenesulfonyl)-3-acryloyloxypropane, 1-(4-hydroxybenzenesulfonyl)-3-methacryloyloxypropane, 1-(4-hydroxybenzenesulfonyl)-2-acryloyloxypropane, 1-(4-hydroxybenzenesulfonyl)- 2-methacryloyloxypropane, 1-(4-hydroxybenzenesulfonyl)-4-acryloyloxybutane, 1-(4-hydroxybenzenesulfonyl)-4-methacryloyloxybutane, 1-(4-hydroxybenzenesulfonyl)-6-acryloyloxyhexane, 1-(4-hydroxybenzenesulfonyl)-6-methacryloyloxyhexane, 1-(4-hydroxybenzenesulfonyl)-8-acryloyloxyoctane, 1-(4-hydroxybenzenesulfonyl)-8-methacryloyloxyoctane, 1-(4-hydroxybenzenesulfonyl)-10-acryloyloxydecane, 1-(4-hydroxybenzenesulfonyl)-10-methacryloyloxydecane, 1-(4-hydroxybenzenesulfonyl)-2-[2-(methacryloyloxyethoxy)]ethane, 1-(4-hydroxybenzenesulfonyl)-3-[3-(methacryloyloxypropoxy)]-propane, 1-(4-hydroxybenzenesulfone)-3-[2,3-bis(methacryloyloxy)]-propane, 1-(3-isopropyl-4-hydroxybenzenesulfonyl)-2-methacryloyloxyethane, 1-(3-isopropyl-4-hydroxybenzenesulfonyl)-2-acryloyloxyethane, 1-(3-isopropyl-4-hydroxybenzenesulfonyl)-3-methacryloyloxypropane, 1-(3-isopropyl-4-hydroxybenzenesulfonyl)-3-acryloyloxypropane, 1-(3-isopropyl-4-hydroxybenzenesulfonyl)-6-methacryloyloxyhexane, 1-(3-isopropyl-4-hydroxybenzenesulfonyl)-6-acryloyloxyhexane, 1-(3-chloro-4-hydroxybenzenesulfonyl)-3-methacryloyloxypropane, 1-(3-chloro-4-hydroxybenzenesulfonyl)-3-acryloyloxypropane, 1-(3-chloro-4-hydroxybenzenesulfonyl)-6-methacryloyloxyhexane, 1-(3-chloro-4-hydroxybenzenesulfonyl)-6-acryloyloxyhexane, 1-(3-chloro-4-hydroxybenzenesulfonyl)-8-methacryloyloxyoctane, 1-(3-chloro-4-hydroxybenzenesulfonyl)-8-acryloyloxyoctane, 1-(3-methyl-4-hydroxybenzenesulfonyl)-6-methacryloyloxyhexane, 1-(3-methyl-4-hydroxybenzenesulfonyl)-6-acryloyloxyhexane, 1-( 3-methyl-4-hydroxybenzenesulfonyl)-8-methacryloyloxyoctane, 1-(3-methyl-4-hydroxybenzenesulfonyl)-8-acryloyloxyoctane, 1-(3-phenyl-4-hydroxybenzenesulfonyl)-3-methacryloyloxypropane, 1-(3-phenyl-4-hydroxybenzenesulfonyl)-3-acryloyloxypropane, 1-(3-phenyl-4-hydroxybenzenesulfonyl)-6-methacryloyloxyhexane, 1-(3-phenyl-4-hydroxybenzenesulfonyl)hexane, 1-(3-phenyl-4-hydroxybenzenesulfonyl)-8-methacryloyloxyoctane, 1-(3-phenyl-4-hydroxybenzenesulfonyl)oxyoctane, 2-chloro-4-[2-($\beta$-methacryloyloxyethoxy)ethylsulfonyl]2-chloro-4-[2-($\beta$-acryloyloxyethoxy)ethylsulfonyl]phenol, 2-methyl-4-[2-($\beta$-methacryloyloxyethoxy)ethylsulfonyl]phenol, 2-methyl-4-[2-($\beta$-acryloyloxyethoxy)ethylsulfonyl]phenol, 2-phenyl-4-[2-($\beta$-methacryloyloxyethoxy)ethylsulfonyl]phenol, 2-phenyl-4-[2-($\beta$-acryloyloxyethoxy)ethylsulfonyl]phenol, 2-isopropyl-4-[2-($\beta$-methacryloyloxyethoxy)ethylsulfonyl]phenol, and 2-isopropyl-4-[2-($\beta$-acryloyloxyethoxy)ethylsulfonyl]phenol.

4. The hydroxybenzenesulfone compound of claim 1, wherein said hydroxybenzenesulfone compound is represented by the following formula (VI):

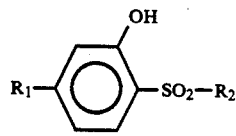

(VI)

wherein $R_1$ and $R_2$ have the same meaning as defined in formula (I) in claim 1.

5. The hydroxybenzenesulfonyl compound of claim 4, wherein said compound is selected from the group consisting of 1-(4-chloro-2-hydroxybenzenesulfonyl)-6-methacryloyloxyhexane and 1-(4-chloro-2-hydroxybenzenesulfonyl)-6-acryloyloxyhexane.

* * * * *